United States Patent
Cohen et al.

(10) Patent No.: US 8,871,808 B2
(45) Date of Patent: Oct. 28, 2014

(54) **OVER-PRODUCTION OF DIHOMO LINOLENIC ACID BY A MUTANT STRAIN OF *PARIETOCHLORIS INCISA***

(75) Inventors: Zvi Cohen, Omer (IL); Inne Khozin-Goldberg, Midreshet Sde Boker (IL); Sammy Boussiba, Omer (IL); Avigad Vonshak, Midreshet Sde Boker (IL)

(73) Assignee: Ben-Gurion University of the Negev Research and Development Authority et al., Be'er Sheva (IL)

(*) Notice: Subject to any disclaimer, the term of this patent is extended or adjusted under 35 U.S.C. 154(b) by 1533 days.

(21) Appl. No.: 11/919,006

(22) PCT Filed: Jun. 21, 2007

(86) PCT No.: PCT/IL2007/000759
§ 371 (c)(1),
(2), (4) Date: Jul. 15, 2011

(65) Prior Publication Data
US 2011/0263708 A1    Oct. 27, 2011

Related U.S. Application Data

(60) Provisional application No. 60/815,589, filed on Jun. 22, 2006.

(51) Int. Cl.
*A01N 37/00* (2006.01)
*C12P 7/64* (2006.01)
*C12N 1/12* (2006.01)
*A23D 9/00* (2006.01)
*C12N 9/02* (2006.01)
*A23L 1/29* (2006.01)
*A23L 1/30* (2006.01)
*C12R 1/89* (2006.01)

(52) U.S. Cl.
CPC .............. *A23D 9/00* (2013.01); *A23V 2002/00* (2013.01); *C12N 9/0083* (2013.01); *C12P 7/6472* (2013.01); *A23L 1/296* (2013.01); *A23L 1/3008* (2013.01); *C12R 1/89* (2013.01)
USPC ........................ 514/560; 435/134; 435/257.1

(58) Field of Classification Search
USPC .................................. 514/560; 435/134, 257.1
See application file for complete search history.

(56) References Cited

U.S. PATENT DOCUMENTS 6,602,690 B2    8/2003    Kawashima et al.

FOREIGN PATENT DOCUMENTS

| EP | 0 195 570 | 9/1986 |
| EP | 0 535 940 | 4/1993 |
| EP | 0 711 503 | 5/1996 |
| WO | 01/84961 | 11/2001 |
| WO | 03/079810 | 10/2003 |

OTHER PUBLICATIONS

International Preliminary Report on Patentability issued for PCT Application No. PCT/IL2007/001012, dated Feb. 16, 2010.
Jareonkitmongkol et al.. "A Novel DELTA-5-desaturase-defective mutant of *Mortierella alpina* 1S-4 and its dihomo-gamma-linolenic acid productivity", Applied and Environmental Microbiology, vol. 59, No. 12, Dec. 1993, pp. 4300-4304, XP002427027 ISSN: 0099-2240.
Kawashima et al., "Industrial Production of dihomo-gamma-linolenic acid by a DELTA 5 desaturase-defective mutant of *Mortierella alpina* 1S-4 fungus", Journal of the American Oil Chemists' Society, vol. 77, No. 11, Nov. 2000, pp. 1135-1138, XP008084822 ISSN: 0003-021X.
Saeree Jareonkitmongkol et al, A Novel Δ5-Desaturase-Defective Mutant of *Mortierella alpina* 1S-4 and Its Dihomo-γ-Linolenic Acid Productivity, Applied and Environmental Microbiology, vol. 59, No. 12, (1993), pp. 4300-4304.
Hiroshi Kawashiima et al., "Industrial Production of Dihomo-γ-linolenic Acid by a Δ5 Desaturase-defective Mutant of *Mortierella alpina* 1S-4 Fungus1" JAOCS, vol. 77, No. 11, (2000), pp. 1135-1138.
Milan Certik et al, "Desaturase-Defective Fungal Mutants: Useful Tools for the Regulation and Overproduction of Polyunsaturated Fatty Acids", TIBTECH, Dec. 1998, vol. 16, pp. 500-505.
Irina A. Guschina et al., "Lipids and Lipid Metabolism in Eukaryotic Algae", Progress in Lipid Research 45, (2006), pp. 160-186.
Sandra D. Dyal et al., "Implications for the Use of *Mortierella* Fungi in the Industrial Production of Essential Fatty Acids", Food Research International 38, (2005), pp. 445-467.
Owen P. Ward et al., "Omega-3/6 Fatty Acids: Alternative Sources of Production", Process Biochemistry 40, (2005), pp. 3627-3652.
Toshihiro Nagao et al., "Enzymatic Purification of Dihomo-γ-Linolenic Acid From *Mortierella* Single-Cell Oil", Journal of Molecular Catalysis B: Enzymatic 44, (2007), pp. 14-19.
Chiara Bigogno et al., "Lipid and Fatty Acid Composition of the Green Oleaginous Alga *Parietochloris incisa*, the Richest Plant Source of Arachidonic Acid", Phytochemistry 60, (2002), pp. 497-503.
Chiara Bigogno et al., "Biosynthesis of Arachidonic Acid in the Oleaginous Microalga *Parietochloris incisa* (*Chlorophyceae*): Radiolabeling Studies", Lipids, vol. 17, No. 2, (2002), pp. 209-216.
International Search Report mailed Nov. 6, 2007.

*Primary Examiner* — Ganapathirama Raghu
(74) *Attorney, Agent, or Firm* — Nixon & Vanderhye P.C.

(57) ABSTRACT

The present invention is primarily directed to a mutant strain of *Parietochloris incisa*, characterized in comprising a substantially reduced intracellular concentration of arachidonic acid (AA) together with a substantially increased intracellular concentration of dihomo-gamma-linolenic acid 20:3ω6 (DGLA).

2 Claims, No Drawings

OVER-PRODUCTION OF DIHOMO LINOLENIC ACID BY A MUTANT STRAIN OF *PARIETOCHLORIS INCISA*

This application is the U.S. national phase of International Application No. PCT/IL2007/000759 filed 21 Jun. 2007 which designated the U.S. and claims priority to Provisional Application No. 60/815,589 filed 22 Jun. 2006, the entire contents of each of which are hereby incorporated by reference.

FIELD OF THE INVENTION

The present invention relates to a process for the production of dihomo-gamma-linolenic acid (DGLA) from microalgae. More specifically, the process includes the cultivation of arachidonic acid-rich microalgae which have lost or significantly reduced their ability for DELTA 5 desaturation

BACKGROUND OF THE INVENTION

DGLA is an industrially-important fatty acid that can be used for pharmaceutical and nutritional applications, in feed for aquaculture and animals and for enhancing their immunological systems thereby reducing their mortality and morbidity due to stress and diseases. DGLA, also known as 8,11, 14-eicosatrienoic acid, is found only in microorganisms and always at low percentages. Usually, it serves as an intermediate in the biosynthesis of arachidonic acid (AA, 20:4$\omega$6), the conversion of DGLA to AA being facilitated by the enzyme $\Delta$5 desaturase.

Microalgae are a "green" and renewable source of biochemicals. They can be cultivated phototrophically or adapted, or engineered for growth under heterotrophic conditions.

Under conditions of nitrogen starvation, the content of AA can reach 21% of dry weight.

Plant oils are capable of producing various PUFAs. However, those produced by higher plants are restricted to chains of up to 18 carbon atoms. Microalgae on the other hand, are known to produce PUFA of up to 22 carbon atoms long.

Both AA and DGLA are PUFA of significant pharmacological interest. DGLA is found in many organisms as an intermediate; however, there are few natural host organisms in which there is accumulation of significant amounts of this PUFA. Possibly the only such source is a $\Delta$5 desaturase deficient mutant of the fungus *Mortierella* (U.S. Pat. No. 6,602, 690). However, one drawback associated with the PUFAs produced by this fungal mutant is the unfavorably low DGLA/AA ratio (approximately 12). A further disadvantage of the fungal-derived PUFAs is that they are susceptible to oxidation and synthetic antioxidants need to be added to prevent deterioration by oxidation. Since the oxidation is a chain reaction, even a small amount of oxygen can destroy PUFA rapidly.

A need thus exists for a natural, "green" source of DGLA that overcomes the aforementioned problems.

SUMMARY OF THE INVENTION

The present invention is primarily directed to a process for producing DGLA, comprising incubating a mutant strain of the microalga *Parietochloris incisa* that is defective in its $\Delta$5 desaturase ($\Delta$5D) gene, and recovering DGLA-containing lipids therefrom. In a preferred embodiment of the invention, the ratio of DGLA to AA (on a weight to weight basis) in the final product (i.e., in the DGLA-containing lipids) is greater than 25. In a particularly preferred embodiment, this ratio is greater than 50.

The present invention is also directed to mutant strains of *Parietochloris incisa*, characterized in comprising a substantially reduced intracellular concentration of AA together with a substantially increased intracellular concentration of DGLA (20:3$\omega$6). As a general guide, the phrase "substantially reduced intracellular concentration of AA", as used in the present context should be taken to mean that said concentration is about 1% of total fatty acids or less. Similarly, the phrase "substantially increased intracellular concentration of DGLA" refers to a DGLA concentration greater than about 30% of total fatty acids.

In one preferred embodiment of the invention, the intracellular concentration of AA is less than 0.1% (w/w), while the intracellular concentration of DGLA is at least 30% (w/w). Both of the aforementioned w/w % concentrations are to be understood as referring to the percentage of the indicated substance in relation to total cellular fatty acids.

In one preferred embodiment, the aforementioned mutant *Parietochloris incisa* strain is a strain which is defective in its $\Delta$5 desaturase ($\Delta$5D) gene. The term "defective" is used in this context to refer to the fact that the $\Delta$5 desaturase ($\Delta$5D) gene is either absent or has substantially less desaturase activity than the wild-type gene due to a point mutation (e.g. a substitution, insertion or deletion of a single nucleic acid base) or a larger mutation (e.g. an inversion or rearrangement of a sequence).

The present invention is particularly directed to Parietochloris incise mutant strain 1 KG-1, which was deposited with Accession No. PTA-8497 at the American Type Culture Collection (ATCC), Manassas, Va., USA, under the terms of the Budapest Treaty.

The present invention is particularly directed to *Parietochloris incisa* mutant strain IKG-1, which was deposited with Accession No. PTA-8497 at the American Type Culture Collection (ATCC), Manassas, Va., USA, under the terms of the Budapest Treaty.

In another; aspect, the present invention is directed to a DGLA-containing lipid, In one preferred embodiment, the ratio of DGLA to arachidonic acid in said lipid is at least 25 parts by weight. In another preferred embodiment of this aspect of the invention, the concentration of DGLA in said DGLA-containing lipid is at least 30% (w/w). In a further preferred embodiment, at least 90% (w/w) of the total lipids in said DGLA-containing lipid are triacylgyerols.

The present invention is further directed to a prostaglandin E1 precursor of algal origin. More specifically, said prostaglandin E1 precursor is obtained from a mutant strain of *Parietochloris incisa*, as characterized hereinabove.

It is to be noted that the term "prostaglandin E1 precursor" is used in this context to refer to any fatty acid or mixture of fatty acids that can serve as a starting material or intermediate in the synthesis of AA. Examples of such fatty acids include GLA and DGLA."

The present invention also provides compositions comprising DGLA-containing lipids and/or prostaglandin E1 precursors, all of which are characterized as described hereinabove. Such compositions may be prepared for use in a variety of applications, including, but not limited to, animal feeds, human infant formulations and food supplements.

In one preferred embodiment of this aspect of the invention, the composition is a health food composition comprising a DGLA-containing lipid according to the present invention.

Said health food composition may be used, inter alia, for alleviating the side effects experienced following alcohol ingestion.

All the abode and other characteristics and advantages of the present indention will be further understood from the following illustrative and non-limitative examples of preferred embodiments thereof.

DETAILED DESCRIPTION

In order to generate mutant strains of *P. incisa* for use in the present invention, the wild-type strain may be exposed to a mutagenic agent and then plated on a solid medium at a low temperature. Colonies that demonstrate decreased growth under these conditions may then be selected and analyzed for their AA and DGLA content.

Cultures of *P. incisa* may be mutagenized by a variety of different techniques including irradiation (e.g. with X-ray or UV light), treatment with chemical mutagens (e.g. 1-methyl-3-nitro-nitrosoguanidine, methanesulfonate and 6-mercaptopurine.

Following mutagenesis, the cells are plated on agar plates, and brought to a low temperature (e.g. 15° C.). Colonies that showed decreased growth can then be isolated and analyzed for lipid content.

The present inventors unexpectedly found that one of the colonies selected as described above proved to be deficient in AA. Under nitrogen starvation conditions the proportion of AA in this Mutant was lower than 1% in comparison to over 50% in the wild; type. However, the proportion of AA's immediate precursor, DGLA (20:3ω6) increased from about 1% in the wild type to over 30% in the mutant. The DGLA/AA ratio in the PUFAs produced by the algal mutant is greater than 25, and in certain circumstances, greater than 50, both of which ratios are clearly superior to the DGLA/AA ratio of 12 associated with PUFAs produced from the fungal mutant described in the aforementioned prior art.

In view of the aforementioned altered DGLA/AA ratio, it may be concluded that the selected mutant strain is defective in its Δ5 desaturase (Δ5D) gene that desaturates DGLA to AA. Similar to the wild type, the mutant is capable of accumulating high contents of lipids, mostly triacylglycerols, under nitrogen starvation, enabling the biotechnological application of the process.

DGLA-rich oil of *P. incisa* mutant is superior to the fungal oil in that it contains β carotene, a natural antioxidant. Fungal PUFAs are susceptible to oxidation and synthetic antioxidants need to be added to prevent deterioration by oxidation. Since the oxidation is a chain reaction, even a small amount of oxygen can destroy PUFA rapidly.

As mentioned hereinabove, in one aspect, the present invention provides compositions comprising DGLA-containing lipids and/or prostaglandin E1 precursors, all of which are characterized as described hereinabove. Such compositions may be prepared for use in a variety of applications including, but not limited to, animal feeds, human infant formulations, food supplements and health food compositions. In addition to the aforementioned DGLA-containing lipids, and/or prostaglandin E1 precursors, said compositions may additionally comprise further active components including pharmaceutically-active and nutraceutically-active agents, as well as fillers, carriers, buffers, bulking agents and other excipients and inactive ingredients as are well known in the art. Further details of excipients that may be used in pharmaceutical and nutraceutical compositions may be found in standard reference works such as Remington's Pharmaceutical Sciences, Mack Publishing Co, Easton, Pa., USA (1980).

The following example is provided for illustrative purposes and in order to more particularly explain and describe the present invention. The present invention, however, is not limited to the particular embodiments or processes disclosed in the example.

EXAMPLE

Mutagenesis

The *P. incisa* strain was isolated from a snow sample of Mt. Oyama (Japan). The microalga has been identified as the chlorophyte *Parietochloris incisa* (Trebouxiophyceae) (Watanabe et al. 1996, *Phycol. Res.* 44: 107-8).

Prior to mutagenesis, cultures were cultivated in BG-11 nutrient medium (Stanier et al., 1971, *Bacteriological Reviews*, 35: 171-205) in 150 mL flasks under controlled temperature and light conditions. The flasks were placed in a temperature regulated shaker at 25° C. and illuminated by cool white fluorescent lights at a light intensity of 115 μmol photon $m^{-2}s^{-1}$ as previously described (Bigogno et al. 2002, *Phytochemistry* 60, 497-503). The cultures were provided with a mixture of air and $CO_2$ (99:1, v/v).

Fifty mL of logarithmically growing cultures were withdrawn and sonicated in 150 mL flasks to segregate the cell clumps. Ten mL of cell suspension, containing mostly single cells, were exposed to the mutagen, 1-methyl-3-nitro-nitrosoguanidine (MNNG) at a final concentration of 100 μg/mL. The stock solution of MNNG was prepared in DMSO (5 mg/mL) to ease the penetration of the mutagen across the tough cell wall of the alga. Following 1 h incubation in an incubator shaker, cells were harvested by centrifugation (1500×g): and washed with mutagen-free BG-11 medium. The washing step was repeated several times. Finally, cells were sonicated in 10 mL of medium and cell numbers of untreated and treated cultures were counted. Cell suspensions were sequentially diluted up to 1000 cells/mL and 50-100 cells were plated, onto Petri dishes with BG-11 agar medium. The resulting cultures were duplicated and incubated under fluorescent light at room and low temperature (15° C.). The percent of survived cells was determined after 10 days. Colonies, which showed poor growth or different appearance at low temperature, were selected for cultivation on liquid BG11 medium in flasks. After sufficient biomass was achieved, cells were transferred onto liquid nitrogen free medium for 14 days, harvested and analyzed for fatty acid composition.

The fatty acid composition of the wild type (WT) and Δ5 desaturase-deficient mutant (MUT) of *P. incisa*, expressed as a wt/wt percentage of total fatty acids is shown in the following tale.

| | Fatty acid composition (% of total FA) | | | | | | | | | | | |
|---|---|---|---|---|---|---|---|---|---|---|---|---|
| Strain | 16:0 | 16:2 ω6 | 18:0 | 18:1 ω9 | 18:1 ω7 | 18:2 | 18:3 ω3 | 18:3 ω6 | 20:3 ω6 | 20:4 ω6 | DGLA/AA | TFA (% DW) |
| WT | 10.9 | 0.6 | 2.8 | 11.0 | 4.3 | 11.1 | 0.9 | 0.9 | 1.2 | 54.6 | 0.02 | 33.3 |
| MUT | 8.0 | 0.2 | 1.9 | 34.4 | 2.9 | 12.8 | 1.2 | 1.1 | 34.4 | 0.1 | 340 | 36.5 |

While specific embodiments of the invention have been described for the purpose of illustration, it will be understood that the invention may be carried out in practice by skilled persons with many modifications, variations and adaptations, without departing from its spirit or exceeding the scope of the claims.

The invention claimed is:

1. A non-naturally occurring mutant strain of *Parietochloris incisa*, characterized in comprising a substantially reduced intracellular concentration of arachidonic acid (AA) together with a substantially increased intracellular concentration of dihomo-gamma-linolenic acid 20:3ω6 (DGLA), wherein the intracellular concentration of AA in relation to total cellular fatty acids is less that 0.1% (w/w), and wherein the intracellular concentration of DGLA is at least 30% (w/w), wherein said strain is strain IKG-1, having a ATCC Accession No. PTA-8497.

2. A process for producing DGLA, comprising incubating a mutant strain of the microalga *Parietochloris incisa* that is defective in its Δ5 desaturase (Δ5D) gene, and recovering DGLA-containing lipids therefrom, wherein the ratio of DGLA to AA in the DGLA-containing lipids is greater than 25:1 by weight, wherein said strain is strain IKG-1, having ATCC Accession No. PTA-8497.

* * * * *